(12) United States Patent
Weickert et al.

(10) Patent No.: US 9,651,469 B1
(45) Date of Patent: *May 16, 2017

(54) ELECTROSTATIC PARTICLE SENSOR

(71) Applicant: General Electric Company, Schenectady, NY (US)

(72) Inventors: John David Weickert, Fairfield, OH (US); Andrew Scott Kessie, Springboro, OH (US); Philip T. Smith, Cincinnati, OH (US); Charles Rickards, Cincinnati, OH (US); James R. Noel, Beverly, MA (US); Gregory Griffin, Mason, OH (US); Joshua Daniel Brown, Hamilton, OH (US)

(73) Assignee: General Electric Company, Schenectady, NY (US)

(*) Notice: Subject to any disclaimer, the term of this patent is extended or adjusted under 35 U.S.C. 154(b) by 0 days.

This patent is subject to a terminal disclaimer.

(21) Appl. No.: 15/375,882

(22) Filed: Dec. 12, 2016

Related U.S. Application Data

(63) Continuation-in-part of application No. 15/007,282, filed on Jan. 27, 2016, and a continuation-in-part of application No. 15/007,289, filed on Jan. 27, 2016.

(51) Int. Cl.
*G01N 15/06* (2006.01)

(52) U.S. Cl.
CPC ...... *G01N 15/0656* (2013.01); *G01N 2291/02416* (2013.01)

(58) Field of Classification Search
CPC ............ G01N 2291/02416; G01N 15/0656
(Continued)

(56) References Cited

U.S. PATENT DOCUMENTS 4,531,402 A * 7/1985 Reif ............... G01N 15/0266
324/454
4,531,486 A * 7/1985 Reif ............... G01N 15/0656
123/198 D (Continued)

FOREIGN PATENT DOCUMENTS

GB          2482480 A      2/2012

OTHER PUBLICATIONS

John David Weickert et al., filed Jan. 27, 2016, U.S. Appl. No. 15/007,289.

(Continued)

*Primary Examiner* — Peter Macchiarolo
*Assistant Examiner* — Nathaniel Kolb
(74) *Attorney, Agent, or Firm* — Pamela A. Kachur

(57) ABSTRACT

The present disclosure is directed to an integrated multi-chip module (MCM) sensor assembly having at least one electrostatic sensor and a circuit board. The electrostatic sensor includes an outer housing with an electrode and an amplifier configured therein. The electrode includes a first end and a second end separated by a predetermined length. The second end includes a sensing face that is substantially flush with an edge of the outer housing. Further, the electrode contains a plurality of electrons configured to respond to one or more charged particles that flow past the sensing face by moving either towards or away from the second end. Thus, the amplifier is electrically coupled to the electrode so as to detect a particle level flowing past the sensing face as a function of the electron movement. Moreover, the circuit board is configured within the outer housing and is electrically coupled to the sensor.

19 Claims, 14 Drawing Sheets

(58) Field of Classification Search
USPC .............................................. 73/28.01, 28.02
See application file for complete search history.

(56) References Cited

U.S. PATENT DOCUMENTS

| | | | |
|---|---|---|---|
| 8,037,738 B2* | 10/2011 | Boehler | G01N 15/0656 73/28.01 |
| 2009/0301058 A1* | 12/2009 | Boehler | G01N 15/0656 60/276 |

OTHER PUBLICATIONS

John David Wetckert et al., filed Jan. 27, 2016, U.S. Appl. No. 15/007,282.

* cited by examiner

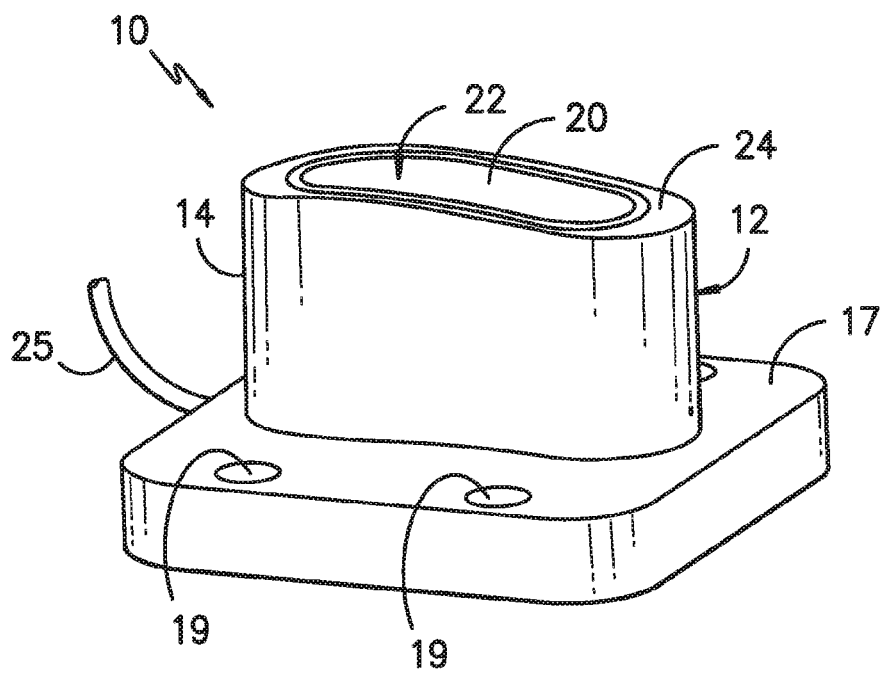
FIG. -1-
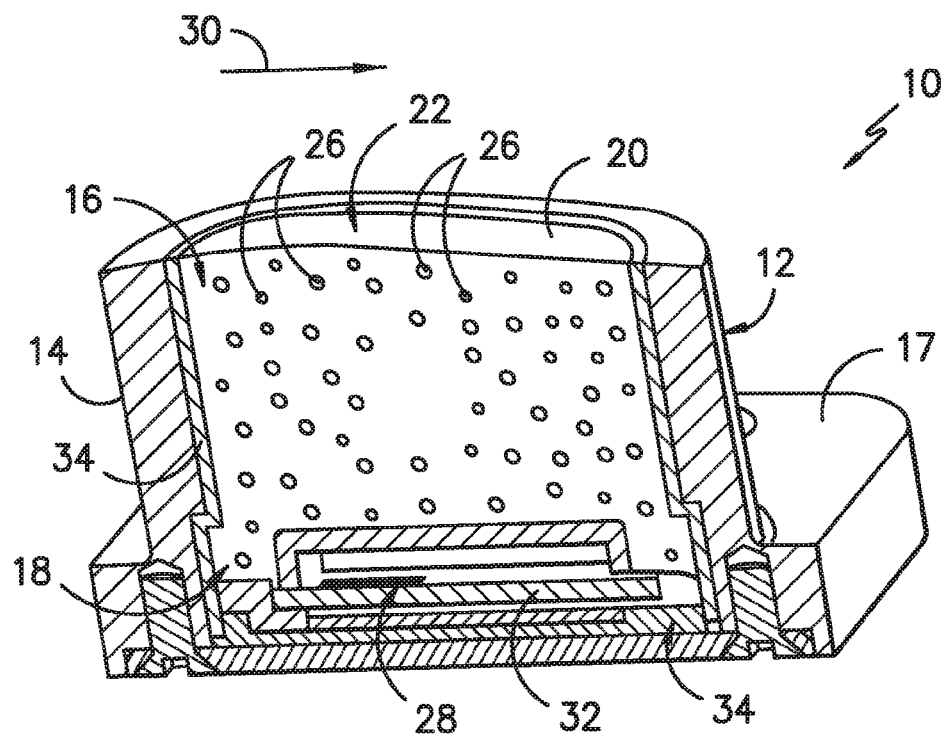
FIG. -2-

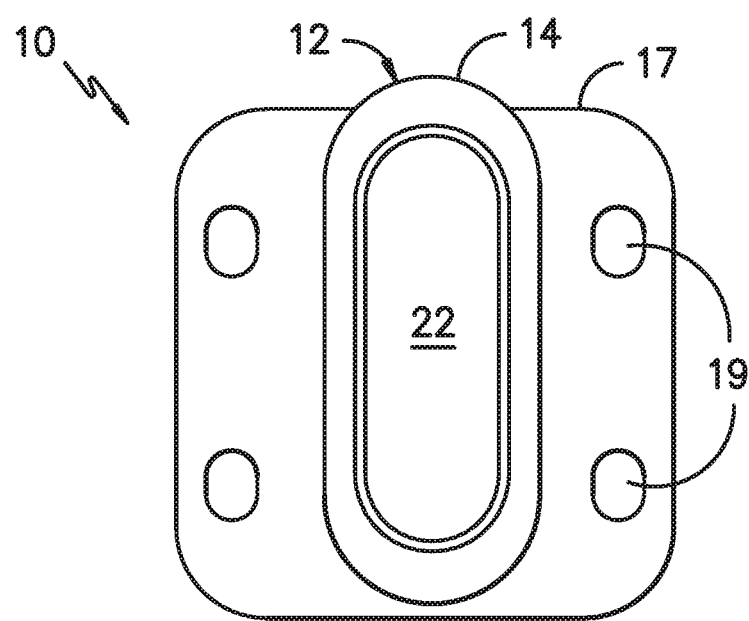
FIG. -3-

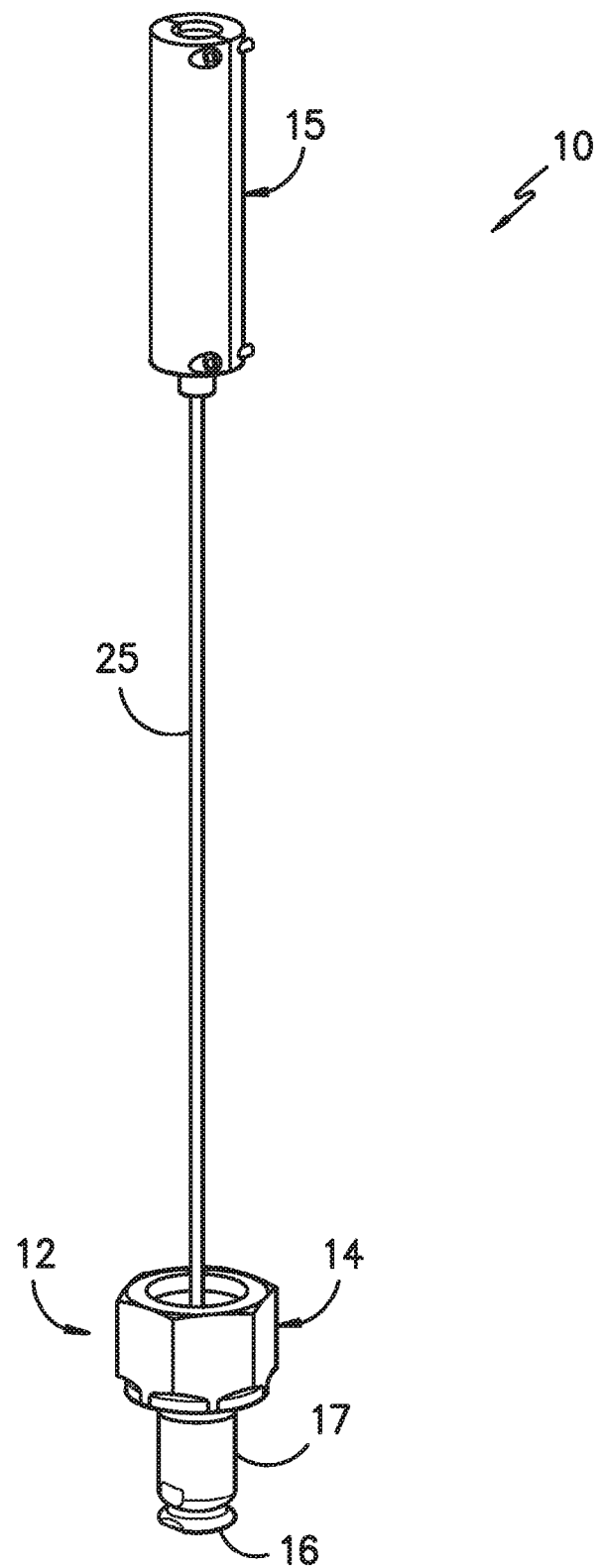
FIG. -4-

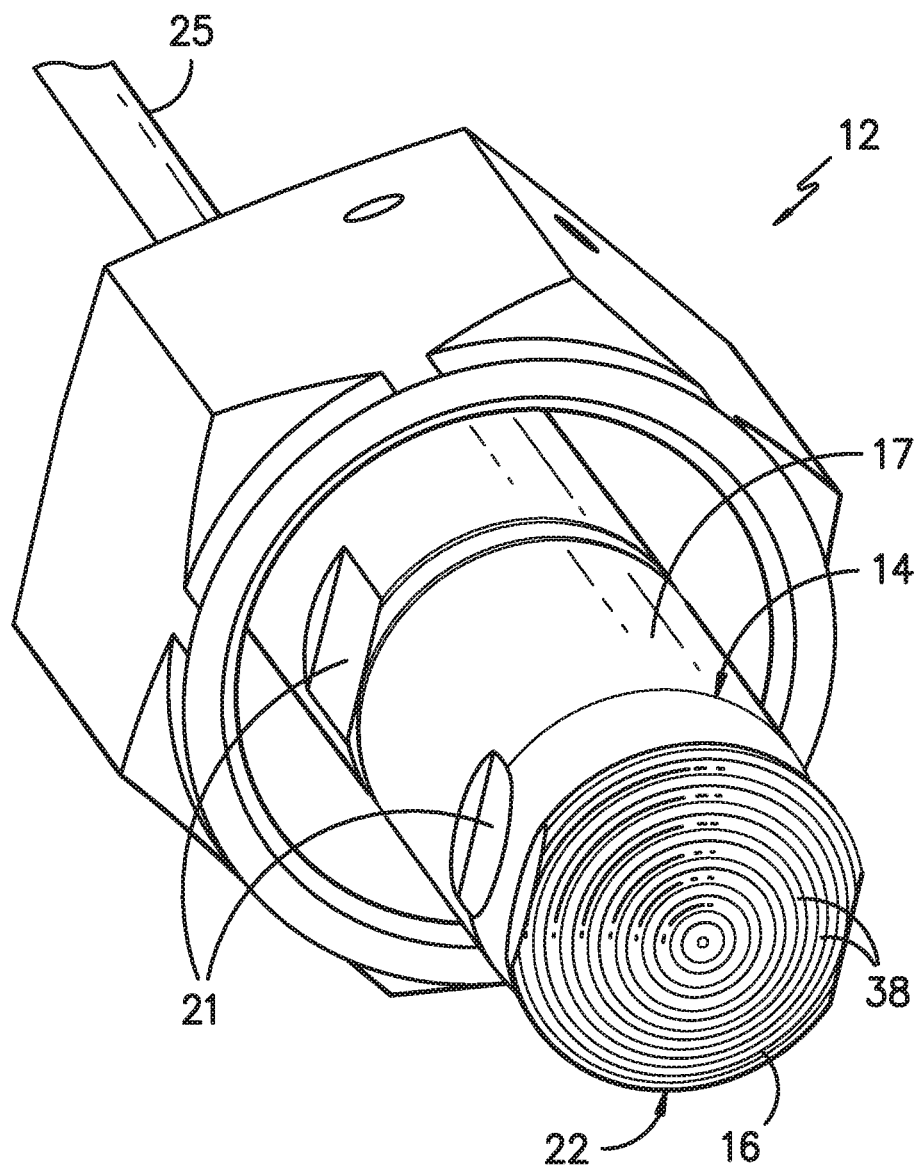
FIG. -5-

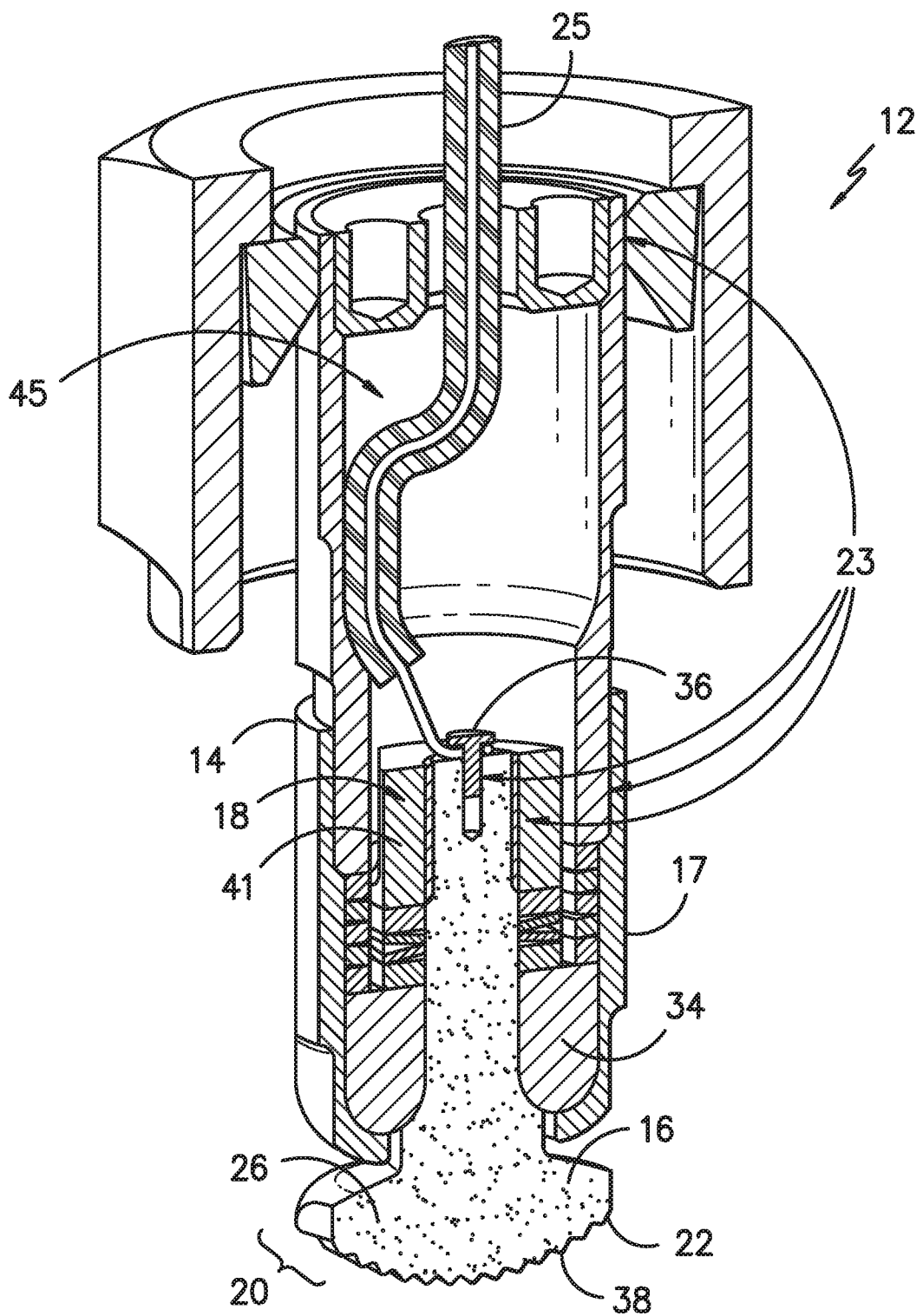
FIG. -6-

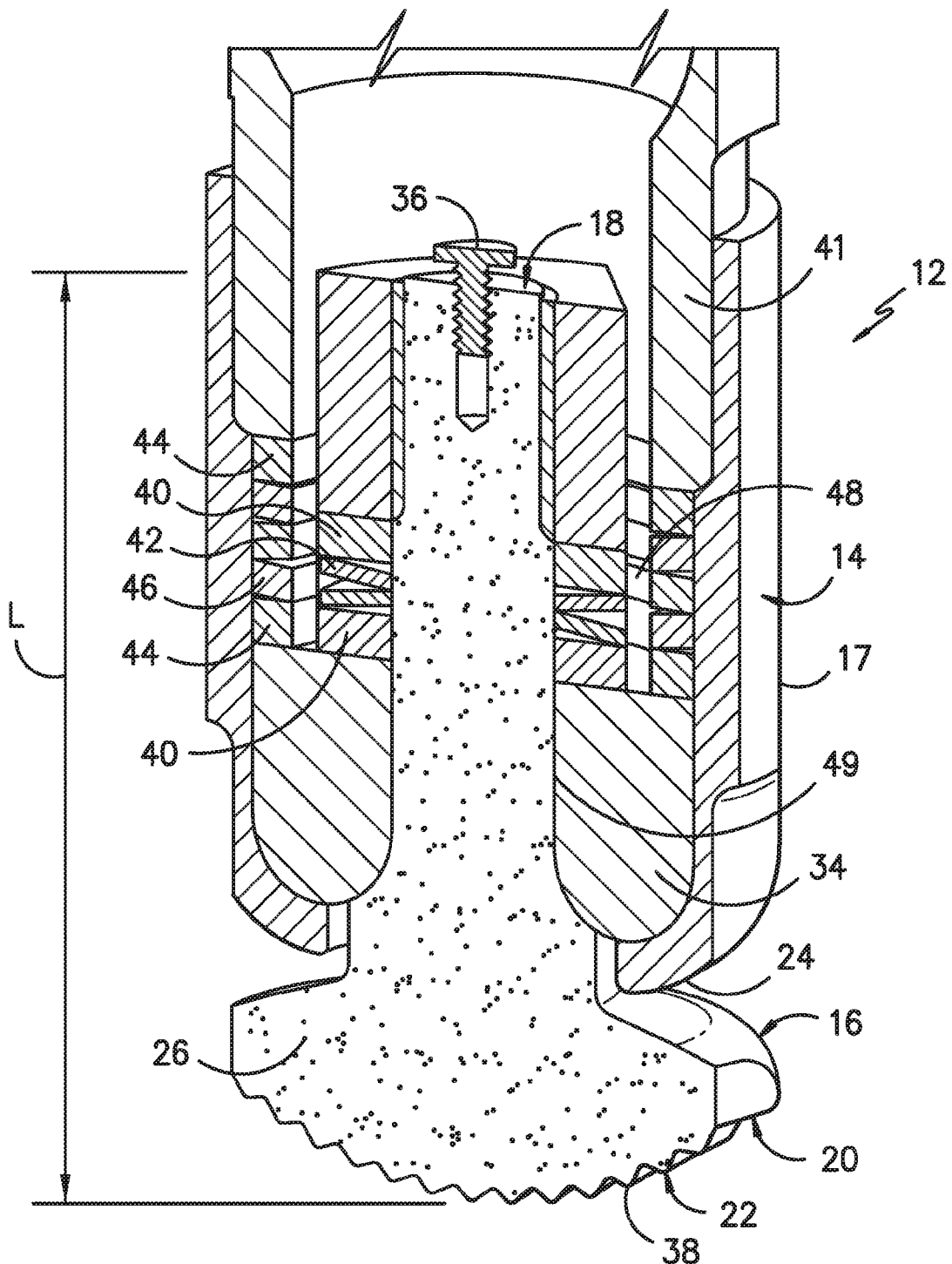
FIG. -7-

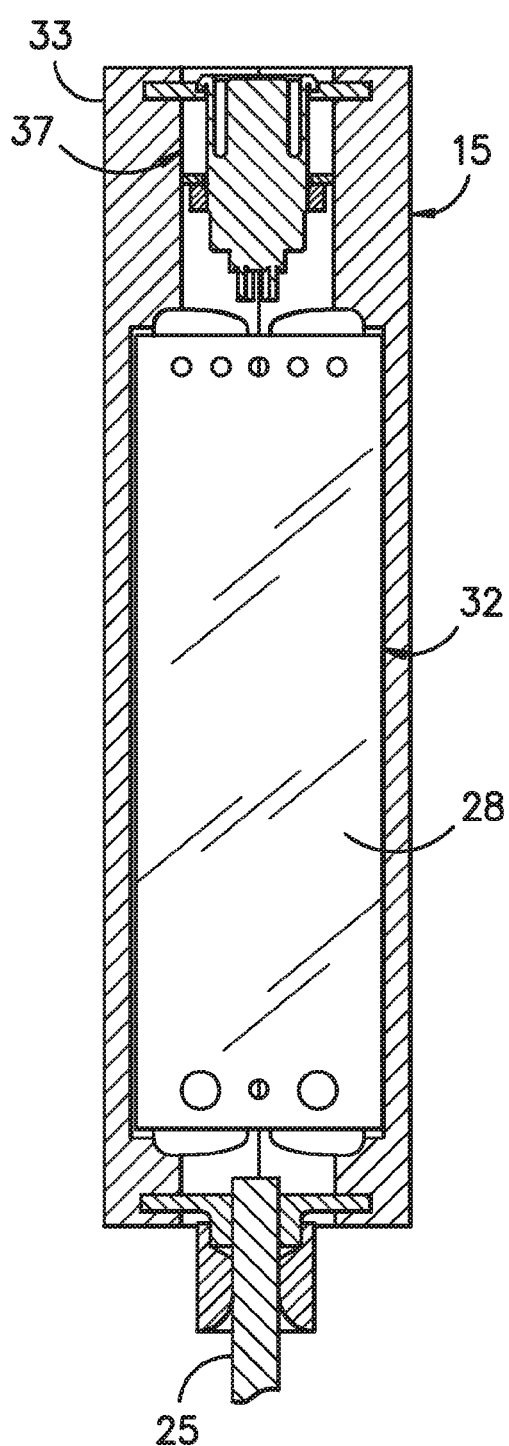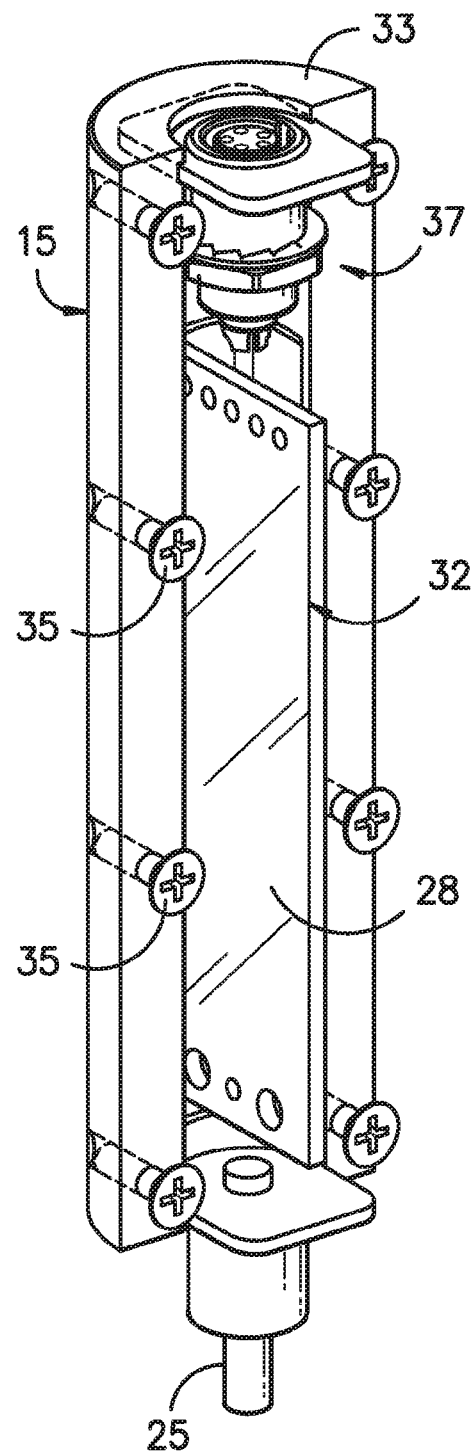
FIG. -8-   FIG. -9-

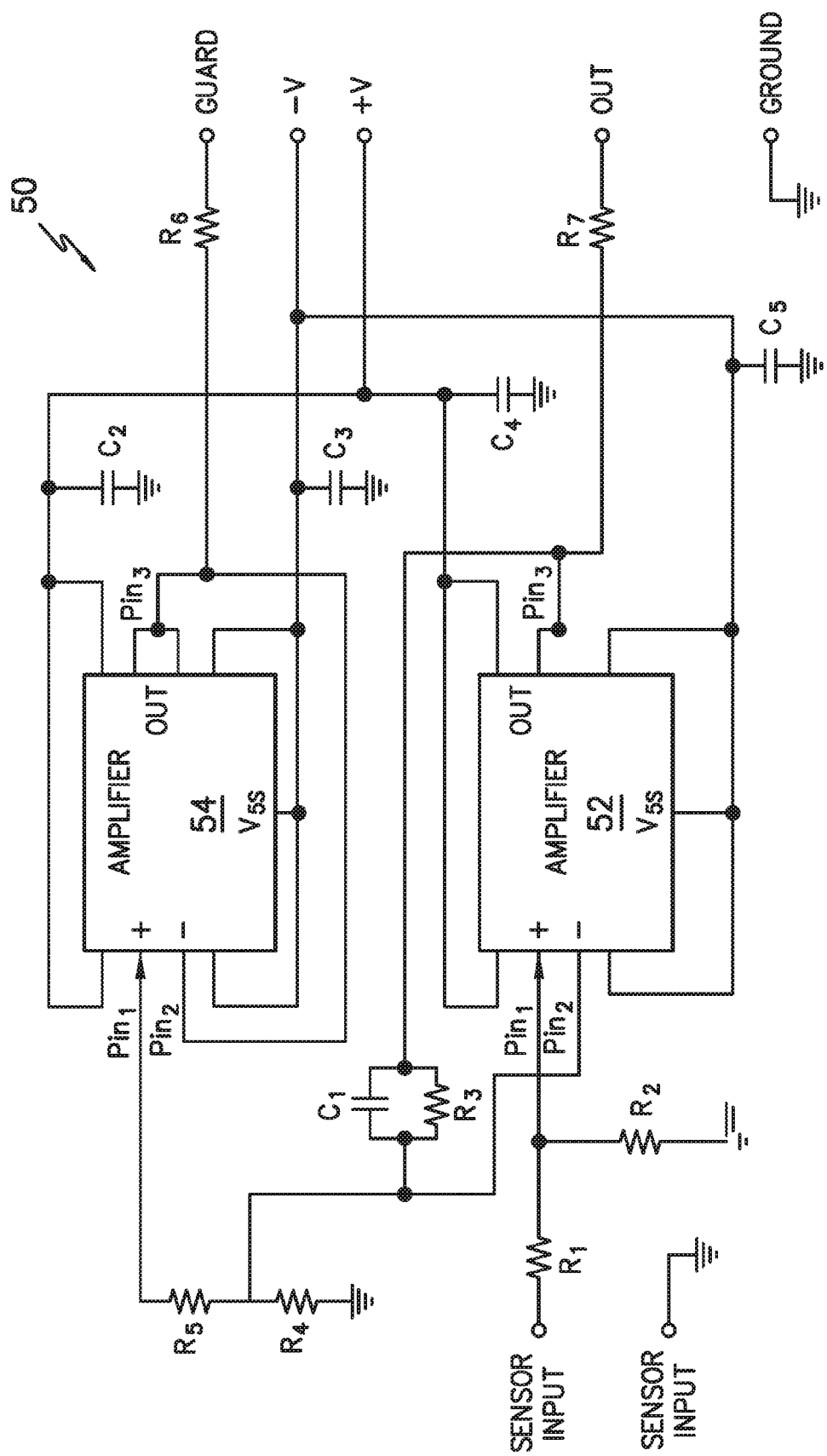
FIG. -10-

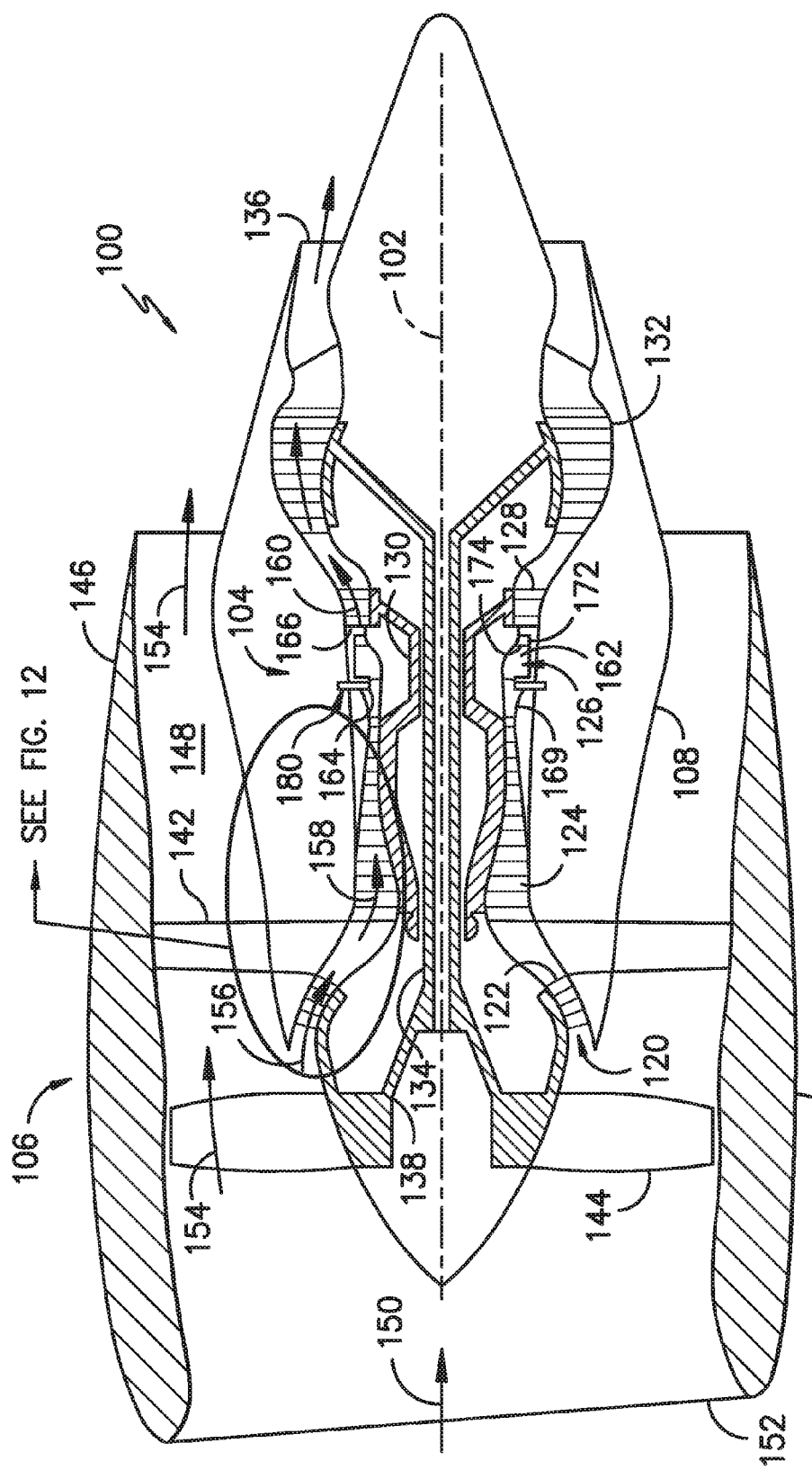
FIG. -11-

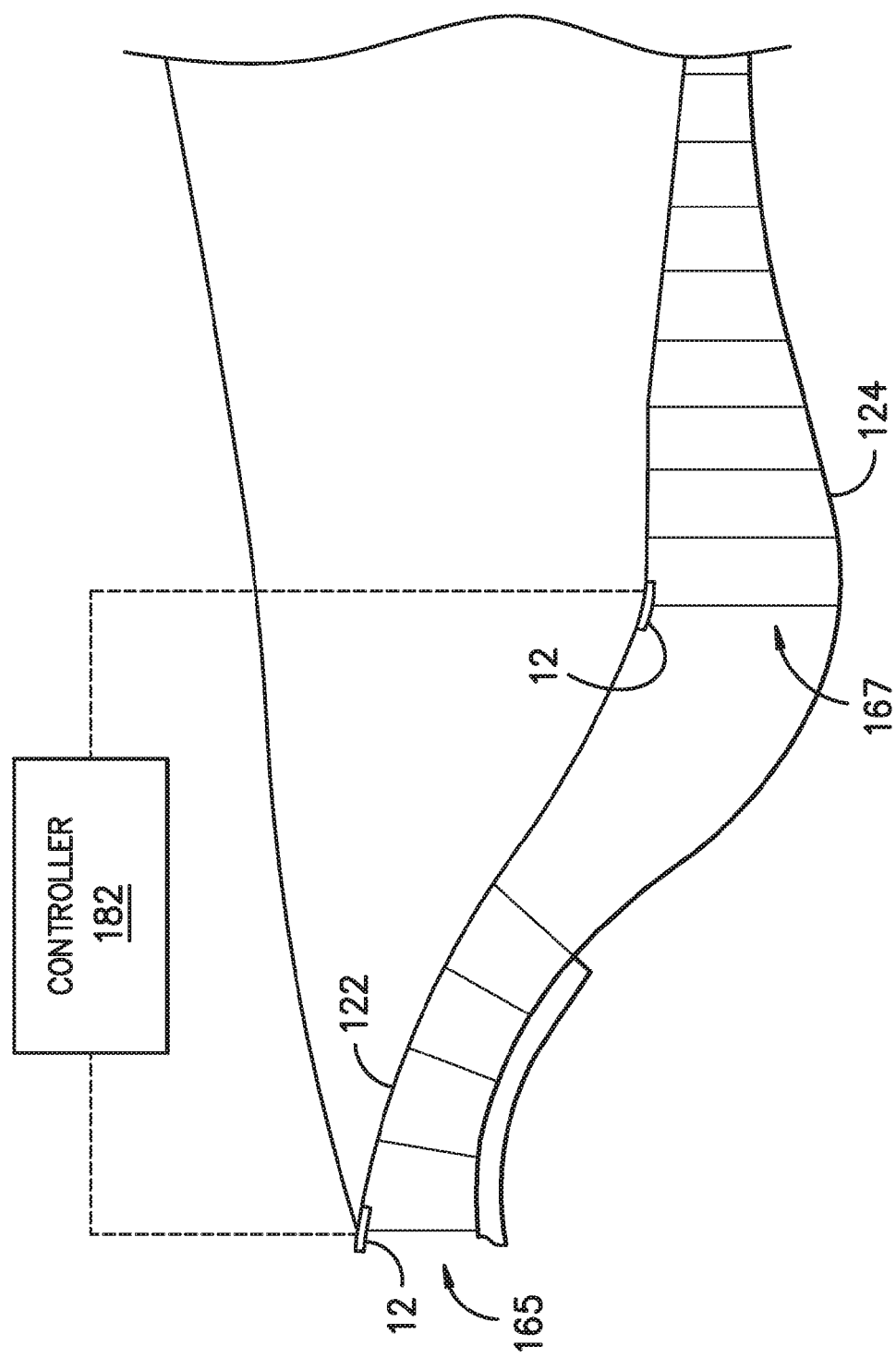

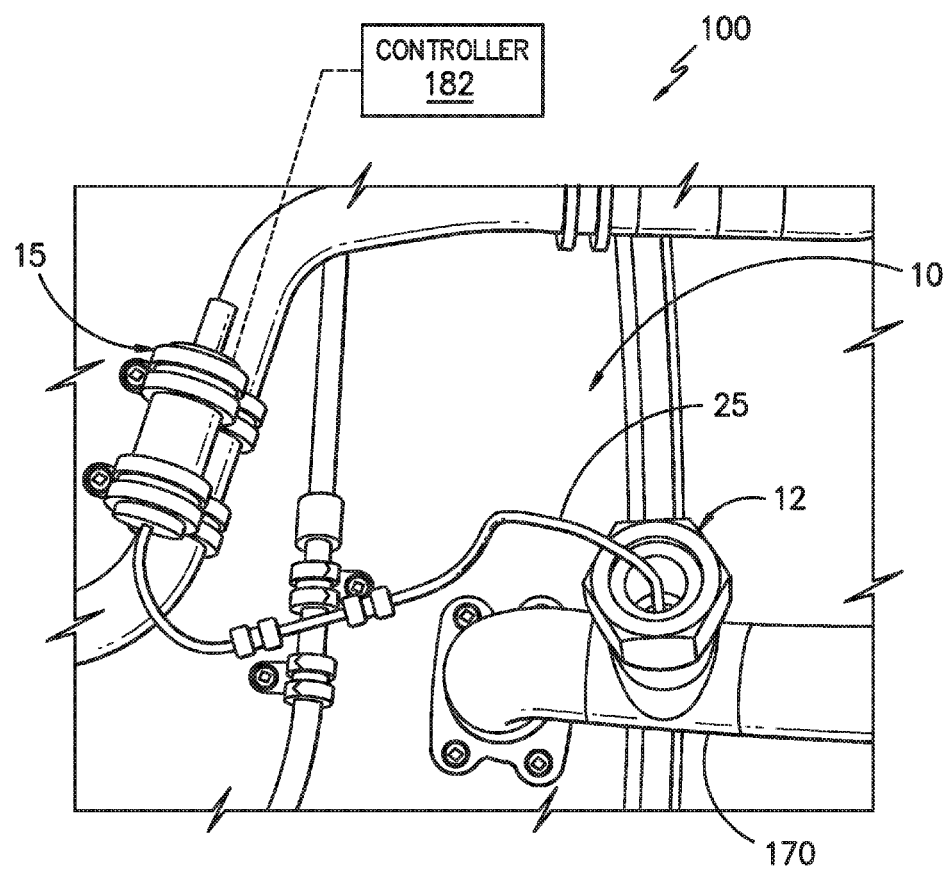
FIG. -13-

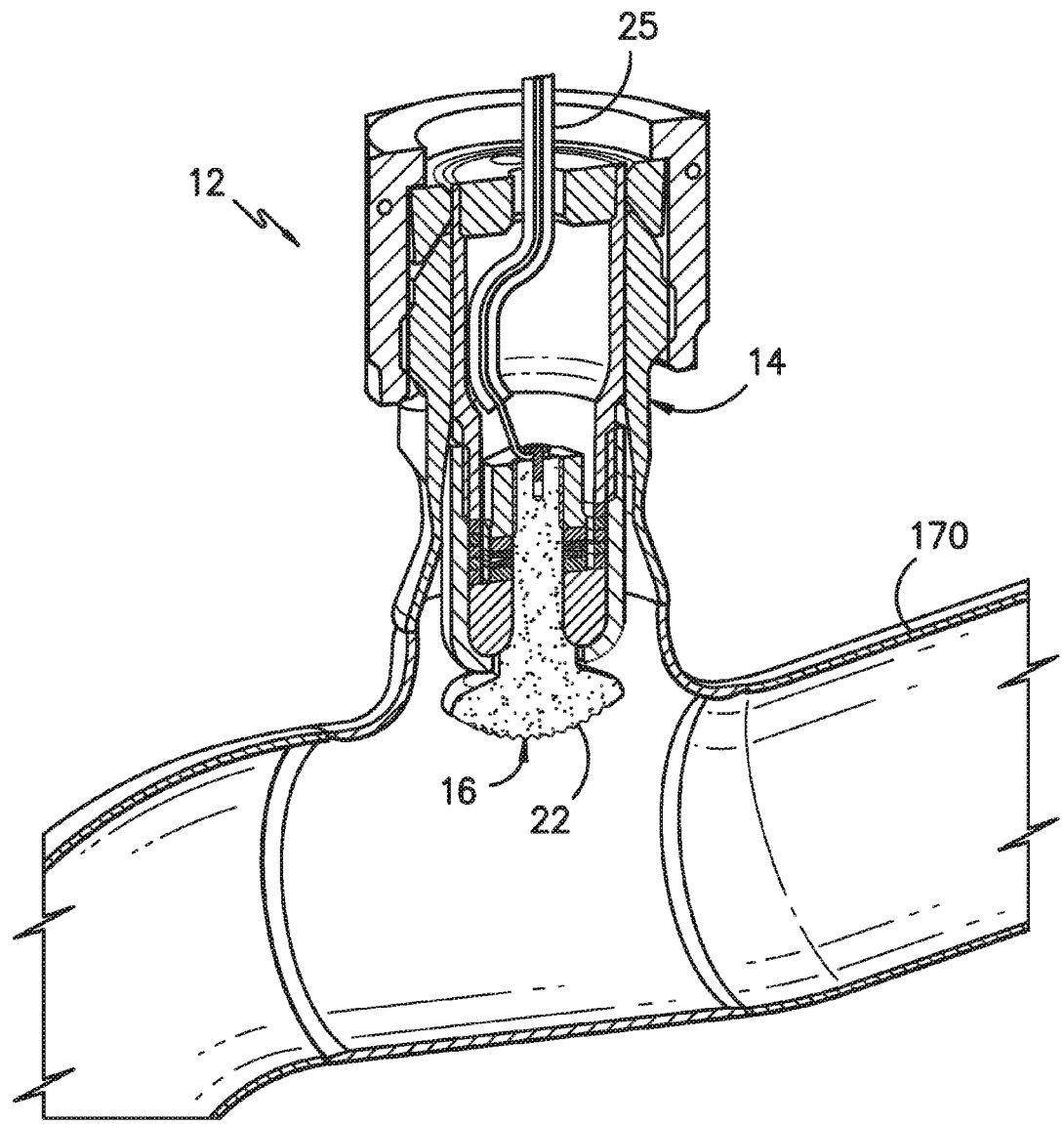
FIG. -14-

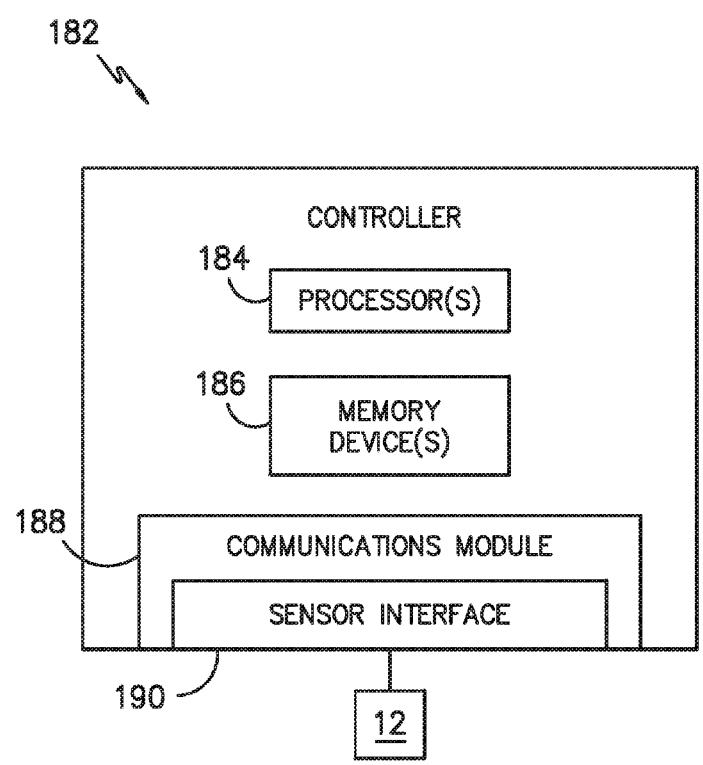
FIG. -15-

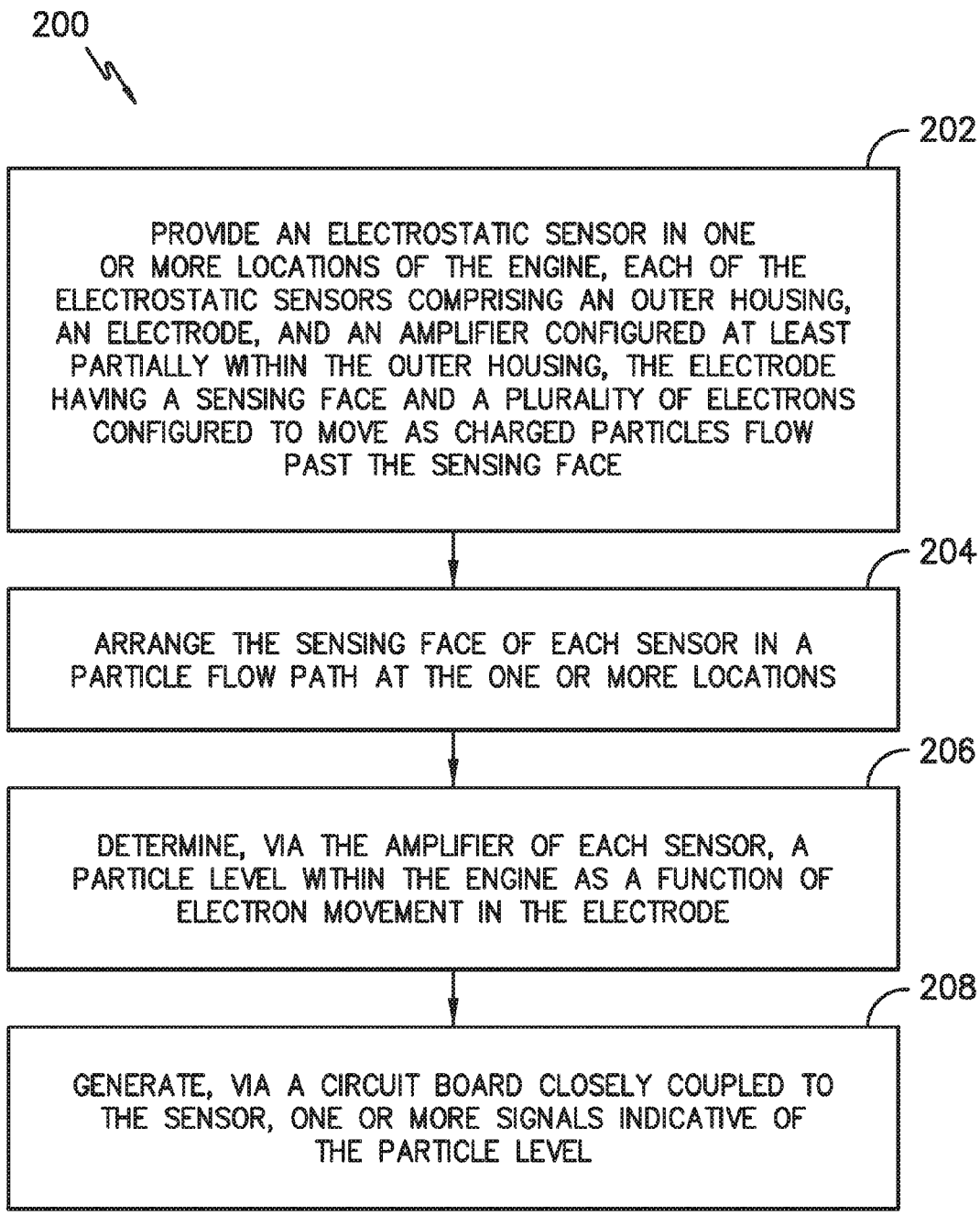
FIG. -16-

ELECTROSTATIC PARTICLE SENSOR

RELATED APPLICATIONS

This application is a continuation-in-part of, and claims the benefit of, U.S. application Ser. No. 15/007,282 filed Jan. 27, 2016, and is a continuation-in-part of, and claims the benefit of, U.S. application Ser. No. 15/007,289, filed Jan. 27, 2016. These applications are herein incorporated by reference in their entirety.

FIELD

The present subject matter relates generally to particle sensors, and more particularly, to electrostatic dust sensors.

BACKGROUND

Many types of engines often require a large supply of clean air to ensure maximum engine performance and engine life and to reduce maintenance requirements. Air cleaning systems have been developed for some types of engines which will remove 99% of the particulate matter drawn into the air intake system. Such high efficiency air cleaning systems are multi-stage units which include barrier type air filters. However, a simple dust leak in the air cleaning system (caused by, for example, accidental perforation of one of the air filters) can negate the effectiveness of the system. In addition, problems with excessively dusty air may be encountered in other types of applications where barrier filters cannot be employed, such as gas turbine engines.

A typical gas turbine engine generally includes, in serial flow order, a compressor section, a combustion section, a turbine section and an exhaust section. In operation, air enters an inlet of the compressor section where one or more axial or centrifugal compressors progressively compress the air until it reaches the combustion section. Fuel is mixed with the compressed air and burned within the combustion section to provide combustion gases. The combustion gases are routed from the combustion section through a hot gas path defined within the turbine section and then exhausted from the turbine section via the exhaust section.

Such gas turbine engines are commonly employed in an aircraft. During operation of the aircraft, the engine environmental particulate and dust ingestion level is a key input to the analytics process, resulting in specific engine-by-engine action. Current environmental dust/particulate level data is provided by ground-based and remote sensing systems separate from the aircraft. Such data has temporal and special variations as well as error, thereby making accurate assessment of engine conditions at takeoff and climb of the aircraft particularly difficult. On the other hand, if sensors are mounted on the engine, the electronics of such sensor systems are typically connected to the individual sensors via a plurality of long cables and connectors. In this case, any motion or vibration of the cabling can produce more signal than the dust particles passing the sensor face, thereby resulting in a poor signal-to-noise ratio. These spurious signals are due to triboelectric and piezoelectric effects of the cables and connectors.

Accordingly, the present disclosure is directed to an improved sensor system that addresses the aforementioned issues. More specifically, the present disclosure is directed to a sensor assembly that includes one or more improved electrostatic sensors having integrated electronics and/or shorter cable connections that more accurately detects dust particles and/or particulates.

BRIEF DESCRIPTION

Aspects and advantages of the invention will be set forth in part in the following description, or may be obvious from the description, or may be learned through practice of the invention.

In one aspect, the present disclosure is directed to an integrated sensor assembly having at least one electrostatic sensor electrically coupled to a circuit board. The electrostatic sensor includes an outer housing containing an electrode and an amplifier therein. The electrode includes a first end and a second end separated by a predetermined length. The second end includes a sensing face that is substantially flush with an edge of the outer housing. Further, as the electrode is a conductor, it contains a plurality of electrons configured to respond to one or more charged particles that flow past the sensing face by moving either towards or away from the second end. Thus, the amplifier is electrically coupled to the electrode so as to detect a particle level flowing past the sensing face as a function of the electron movement. Moreover, the circuit board is configured within the outer housing and is electrically coupled to the sensor.

In another aspect, the present disclosure is directed to a multi-chip module (MCM) sensor assembly. The MCM sensor assembly includes at least one electrostatic sensor. More specifically, the electrostatic sensor may include an outer housing containing an electrode and an amplifier. The electrode includes a first end and an opposing second end having a sensing face. Further, the electrode contains a plurality of electrons configured to respond to one or more charged particles that flow past the sensing face by moving either towards or away from the second end. The amplifier is electrically coupled to the electrode so as to detect a particle level flowing past the sensing face as a function of the electron movement. Moreover, the circuit board is electrically coupled to the sensor. It should be understood that the MCM sensor assembly may be further configured with any of the additional features as described herein.

In yet another aspect, the present disclosure is directed to a sensor assembly. The sensor assembly includes at least one electrostatic sensor. More specifically, the electrostatic sensor may include an outer housing containing an electrode configured at least partially within the outer housing. The electrode includes a first end and a second end separated by a predetermined length. The first end is secured within the outer housing and the second end includes a sensing face that extends beyond an edge of the outer housing. Further, the electrode includes a plurality of electrons configured to respond to one or more charged particles that flow past the sensing face by moving either towards or away from the second end. The electrostatic sensor also includes an amplifier configured within the outer housing and electrically coupled to the electrode. Further, the amplifier is configured to detect a particle level flowing past the sensing face as a function of electron movement. In addition, the electrostatic sensor includes a circuit board electrically coupled to the sensor via a cable. It should be understood that the sensor assembly may be further configured with any of the additional features as described herein.

These and other features, aspects and advantages of the present invention will become better understood with reference to the following description and appended claims. The accompanying drawings, which are incorporated in and constitute a part of this specification, illustrate embodiments of the invention and, together with the description, serve to explain the principles of the invention.

BRIEF DESCRIPTION OF THE DRAWINGS

A full and enabling disclosure of the present invention, including the best mode thereof, directed to one of ordinary skill in the art, is set forth in the specification, which makes reference to the appended figures, in which:

FIG. 1 illustrates a perspective view of one embodiment of a MCM sensor assembly according to the present disclosure, particularly illustrated an electrostatic sensor thereof having integrated electronics configured therein;

FIG. 2 illustrates a cross-sectional view of the electrostatic sensor of FIG. 1;

FIG. 3 illustrates a top view of the electrostatic sensor of FIG. 1;

FIG. 4 illustrates a perspective view of another embodiment of a MCM sensor assembly according to the present disclosure, particularly illustrating an electrostatic sensor thereof coupled to an electronics housing via a cable;

FIG. 5 illustrates a detailed perspective view of one embodiment of the electrostatic sensor of the MCM sensor assembly of FIG. 4;

FIG. 6 illustrates a cross-sectional view of the electrostatic sensor of the MCM sensor assembly of FIG. 5;

FIG. 7 illustrates a detailed cross-sectional view of the electrostatic sensor of the MCM sensor assembly of FIG. 6;

FIG. 8 illustrates a front view of the electronics housing of the MCM sensor assembly of FIG. 4;

FIG. 9 illustrates a side perspective view of the electronics housing of the MCM sensor assembly of FIG. 4;

FIG. 10 illustrates a schematic diagram of one embodiment of the circuit topology of the MCM sensor assembly according to the present disclosure;

FIG. 11 illustrates a schematic cross-sectional view of one embodiment of a gas turbine engine according to the present disclosure;

FIG. 12 illustrates a simplified schematic diagram of the gas turbine engine of FIG. 11, particularly illustrating sensor locations for one embodiment of the MCM sensor assembly according to the present disclosure;

FIG. 13 illustrates a perspective view of the gas turbine engine of FIG. 11, particularly illustrating additional sensor locations for another embodiment of the MCM sensor assembly according to the present disclosure;

FIG. 14 illustrates a cross-sectional perspective view of one embodiment of the MCM sensor assembly according to the present disclosure, particularly illustrating the sensor assembly mounted on a compressor bleed pipe of a gas turbine engine;

FIG. 15 illustrates a block diagram of one embodiment of suitable components that may be included in a controller of an engine according to the present disclosure; and FIG. 16 illustrates a flow diagram of one embodiment of method for detecting particles in an engine according to the present disclosure.

DETAILED DESCRIPTION

Reference now will be made in detail to embodiments of the invention, one or more examples of which are illustrated in the drawings. Each example is provided by way of explanation of the invention, not limitation of the invention. In fact, it will be apparent to those skilled in the art that various modifications and variations can be made in the present invention without departing from the scope or spirit of the invention. For instance, features illustrated or described as part of one embodiment can be used with another embodiment to yield a still further embodiment. Thus, it is intended that the present invention covers such modifications and variations as come within the scope of the appended claims and their equivalents.

As used herein, the terms "first", "second", and "third" may be used interchangeably to distinguish one component from another and are not intended to signify location or importance of the individual components.

The terms "upstream" and "downstream" refer to the relative direction with respect to fluid flow in a fluid pathway. For example, "upstream" refers to the direction from which the fluid flows, and "downstream" refers to the direction to which the fluid flows.

Generally, the present disclosure is directed to a sensor assembly having at least one electrostatic sensor electrically coupled to a circuit board. In certain embodiments, the sensor assembly is designed as a function of the temperature of the application environment. For example, in one embodiment, the location of the electrostatic sensor may be cool enough such that the sensor circuit can be implemented with low temperature discrete electronic parts on a circuit board. Alternatively, in further embodiments, where the temperatures are higher, the sensor assembly may include an integrated MCM sensor assembly. As such, the MCM sensor assembly of the present disclosure may be used in a plurality of applications, such as an aircraft gas turbine engine, as well as any other suitable engine types. For example, it should be understood that the MCM sensor assembly and related methods are also suitable for any other type of engine, including but not limited to an industrial engine, a power generation engine, a land-based engine, a marine engine, or similar. More specifically, the electrostatic sensor includes an outer housing containing an electrode and an amplifier configured at least partially therein. Further, the electrode includes a first end and a second end separated by a predetermined length. The first end may be secured within the outer housing, whereas the second end may include a sensing face that is either flush with an edge of the outer housing or may extend within or past the edge of the outer housing. Further, as the electrode is a conductor, it contains a plurality of electrons configured to respond to one or more charged particles that flow past the sensing face by moving either towards or away from the second end. Thus, the amplifier is electrically coupled to the electrode so as to detect a particle level flowing past the sensing face as a function of the electron movement. Moreover, the circuit board is electrically coupled to the sensor either by being housed within the outer housing or connected to the sensor via a shortened cable.

Thus, the outer housing of the sensor and the electronics configuration minimizes the distance between the sensor input and the electrode, thereby increasing sensitivity of the sensor. As such, the present disclosure provides various advantages not present in the prior art. For example, the electrostatic sensors of the present disclosure provide more accurate particle detection that is robust and reliable. Further, since the electronics are integrated within the sensor or closely coupled thereto, the present design requires less maintenance and suffers from fewer operational issues over prior art designs. Moreover, the amplifier low leakage current facilitates direct current (DC) coupling of the amplifier, which allows low frequency changes in particle levels to be captured. In addition, the high input impedance of the electrode improves the sensor's sensitivity to small changes in charge in the sensing face. Further, the high input impedance of the electrode also improves the low frequency response of the sensor by preventing the charge redistribution within the electrode caused by the sensed particles from leaking away such that an output signal cannot be produced. Thus, the electrostatic sensor of the present disclosure is capable of detecting from about one (1) part in seven (7) million by mass of particles. As such, the electrostatic sensor of the present disclosure is configured to detect dust, debris, airborne particulates, ice (i.e. very fine ice crystals), sand, volcanic ash, and/or any other particles within a fluid medium such as air, water, oil, fuel, and/or similar. In addition, the electrostatic sensor, when located in an engine exhaust nozzle, can also detect internally generated particles from rubs of internal engine parts and/or deterioration of engine parts which results in the release of debris. For example, such detection is accomplished by sensing the "natural charge" accumulation on the particles as they pass thru the engine. Thus, the integrated electronics/integral cable connections increase sensor sensitivity to the very small "natural charges" of the particles over prior art.

Referring now to the drawings, FIGS. 1-9 and 13-14 illustrate various embodiments of a MCM sensor assembly 10 according to the present disclosure. As used herein, a MCM generally refers to an electronic assembly (such as a package with a number of conductor terminals or "pins") where multiple integrated circuits (ICs), semiconductor dies, and/or other discrete die components are integrated, usually onto a unifying substrate, so that in use it is treated as if it were a single component. More specifically, as shown in FIGS. 1-3, one embodiment of an integrated MCM assembly 10 is illustrated. For example, FIG. 1 illustrates a perspective view of integrated MCM assembly 10; FIG. 2 illustrates a cross-sectional view of the integrated MCM assembly 10; and FIG. 3 illustrates a top view of integrated MCM assembly 10. FIGS. 4-9 illustrate another embodiment of an MCM sensor assembly 10, wherein the electronics are closely coupled together via a shortened cable 25 but not integrated.

Referring particularly to FIGS. 1-3, the integrated MCM assembly 10 includes at least one electrostatic sensor 12 having an outer housing 14 or casing. More specifically, as shown, the outer housing 14 may include a base or mounting portion 17 configured for mounting or otherwise securing the sensor 12 into a desired location. For example, as shown in FIGS. 1 and 3, the mounting portion 17 of the sensor 12 may include one or more through holes 19 configured for mounting the electrostatic sensor(s) 12 at the desired location(s). More specifically, in certain embodiments, each of the through holes 19 may be configured to receive a fastener (e.g. a threaded bolt) so as to secure the sensors 12 at the desired location(s). Alternatively, the electrostatic sensor(s) 12 may be secured or mounted via any other suitable methods, including but not limited to metal clips, clamps, welded nichrome foil, welding, or similar.

Further, as shown, the electrostatic sensor 12 contains an electrode 16 configured within the outer housing 14. The electrode 16 includes a first end 18 and a second end 20 separated by a predetermined length L. In certain embodiments, the predetermined length L may be set by geometry constraints of the engine installation. For example, in one embodiment, the predetermined length L may be from about one inch to about three inches to allow the electrons 26 to migrate in the electrode 16 and therefore be detectable by the amplifier 28 (which is discussed below). In addition, as shown, the electrode 16 includes a plurality of electrons 26 configured to move as charged particles flow past the sensing face 22 as indicated by arrow 30. As such, the predetermined length L allows the electrons 26 to easily flow towards and/or away from the sensing face 22 depending on the charge of the particles flowing thereby. Further, the first end 18 of the electrode 16 is generally secured within the outer housing 14, whereas the second end 20, which includes the sensing face 22, may be flush with an edge 24 of the outer housing 14. Moreover, as shown in FIGS. 1 and 2, the sensing face 22 of the electrode 16 may include a curved surface having a predetermined radius.

In addition, as shown in the illustrated embodiment, the electrostatic sensor 12 may include at least one amplifier 28 configured within the outer housing 14 that is electrically coupled to the electrode 16. In such embodiments, the amplifier 28 may have an operating temperature range of from about −55 degrees Celsius (° C.) to about 250° C., more preferably from about 150° C. to about 230° C. More specifically, the amplifier 28 may include a silicone on insulator (SOI) operational amplifier. For example, in certain embodiments, the amplifier 28 of the present disclosure may include the wideband SOI operational amplifier manufactured by Honeywell, Inc. of Plymouth, Minn., USA. Such amplifiers have extremely low leakage current and are capable of operating at high temperatures. As such, the amplifier 28 of the present disclosure is configured to detect or measure a particle level passing by the sensing face 22 as a function of the electron movement.

Further, the MCM assembly 10 may include an integrated circuit board 32 configured within the outer housing 14 and electrically coupled to the sensor 12, e.g. via the amplifier 28. More specifically, as shown, the circuit board 32 may be configured adjacent to the electrode 16 and opposite the sensing face 22. In additional embodiments, the circuit board 32 may be located at any suitable location within the outer housing 14 of the sensor 12. Further, the circuit board 32 as described herein may include any suitable circuit board that mechanically supports and electrically connects the electronic components within the outer housing 14 of the sensor(s) 12. More specifically, certain circuit boards of the present disclosure may include conductive tracks, pads, and/or other features etched from sheets of metal, such as copper, that are laminated onto a non-conductive substrate. Further, the circuit board 32 of the present disclosure may be single-sided, double-sided, or multi-layered. Thus, the circuit board 32 as described herein may be configured to send one or more signals to a controller 182 that are indicative of the particle level passing the sensing face 22, which is described in more detail below.

Referring particularly to FIG. 2, the electrostatic sensor(s) 12 may also include one or more insulators or insulation layers 34. For example, as shown, the electrostatic sensor(s) 12 may include one or more insulation layers 34 configured between the electrode 16 and the outer housing 14. In addition, the electrostatic sensor(s) 12 may include one or more insulation layers 34 within the mounting portion 17 thereof so as to insulate the sensor components from an operating environment. It should further be understood that any number of insulation layers may be employed at any suitable location within the sensor 12.

Referring now to FIG. 4-9, another embodiment of an MCM sensor assembly 10 of the present disclosure is illustrated. More specifically, as shown in FIG. 4, the MCM assembly 10 includes at least one electrostatic sensor 12 coupled to an electronics housing 15 via a cable 25. Further, as shown in FIGS. 4-7, the electrostatic sensor 12 has an outer housing 14 or casing. More specifically, as shown, the outer housing 14 may include a mounting portion 17 configured for mounting or otherwise securing the sensor 12 into a desired location. For example, as shown in FIGS. 5-7, the mounting portion 17 of the sensor 12 may include a threaded outer surface or a B-nut configured for securing or installing the electrostatic sensor(s) 12 in a desired location. Further, as shown in FIGS. 5 and 6, the outer housing 14 of the sensor 12 may also include one or more wrenching flats 21 configured to aid in sensor assembly and/or disassembly as well as installation. In addition, as shown in FIG. 6, the various components of the sensor 12 may be easily secured together via one or more threaded joints 23.

Further, as generally shown in FIGS. 4-7, the electrostatic sensor 12 has an electrode 16 configured at least partially within the outer housing 14. More specifically, as shown in FIG. 7, the electrode 16 includes a first end 18 and a second end 20 separated by a predetermined length L. As such, the electrode 16 is configured to act as an "electron lake" on which the passing charged particles move electrons "in the lake" either towards or away from the electrode second end 20 based on their charge. This shift of electron distribution within the electrode 16 is detected by the amplifier 28. Such a feature therefore is configured to extend the low frequency bandwidth of the sensor 12 below one (1) Hertz (Hz). More specifically, the first end 18 is secured within the outer housing 14, whereas the second end 20 includes a sensing face 22 that extends beyond an edge 24 of the outer housing 14. For example, as shown, the first end 18 is secured within the outer housing 14 via at least one fastener, e.g. nut 41. It should be understood that the first end 18 of the electrode 16 may be further secured using any other suitable means. In addition, as shown in FIGS. 6 and 7, the cable 25 may extend into the sensor 12 through an open cavity 45 and secured and/or electrically coupled to the sensor 12 via fastener 36. More specifically, the outer sheath of the cable 25 may be grounded to the body of the sensor 12 via welded nichrome strips, whereas the inner conductor of the cable 25 may be attached to the sensor 12 via the fastener 36.

Moreover, as shown in FIGS. 5-7, the sensing face 22 of the electrode 16 may include a curved surface having a predetermined radius. In certain embodiments, the predetermined radius is introduced to increase the surface area of the sensing face 22 and/or to increase the sensors gain. Thus, in particular embodiments, the radius may depend on the room available where the sensor assembly 10 is to be installed. In one embodiment, for example, it may be desirable to introduce a radius that increases the surface area of the sensing face 22 by about 50% if possible over a flat sensing face. Such a sensor requires more installation volume, but will be able to detect particles at lower concentration levels.

Further, as shown, the curved surface of the sensing face 22 may have a sculpted profile having one or more protrusions 38. For example, as shown, the protrusions 38 correspond to arcuate ridges that increase the surface area of the sensing face 22 by about 50%. In further embodiments, it should be understood that the curved surface and/or the protrusions 38 may be configured to increase the surface area of the sensing face 22 by less than 50% or more than 50%. As such, the curved surface and/or the protrusions 38 are configured to maximize the area presented to the flow stream of the sensor 12 so as to increase the sensitivity of the sensor 12. It should be understood that the protrusions 38 of the sensing face 22 described herein may further have any suitable shape and/or size so as to increase the sensitivity of the sensor 12.

In addition, as shown in FIGS. 6 and 7, the electrode 16 of the sensor 12 includes a plurality of electrons 26 configured to move as charged particles flow past the sensing face 22. Thus, the electrons 26 are configured to move or flow as charged dust particles flow past the sensing face 22. More specifically, the electrons 26 move within the electrode 16 either towards or away from the sensing face 22 based on the charge of the passing particles.

Referring particularly to FIGS. 4 and 8-9, the electronics housing 15 of the MCM sensor assembly 10 is separate from the electrostatic sensor 12 but still closely coupled thereto via the cable 25. More specifically, in certain embodiments, the cable 25 length may range from about 10 inches to about 48 inches, more preferably from about 12 inches to about 24 inches. As such, even when the electronics are not integrated within the outer housing 14, they are still closely coupled to the sensor components so as to provide increased sensitivity to the sensor 12. Further, the cable 25 may be any suitable electrical cable configured for electrically coupling the sensor 12 to the suitable electronics within the electronics housing 15. For example, in certain embodiments, the cable 25 is a coaxial cable. More specifically, in certain embodiments, the cable 25 may include an integral mineral insulated hardline cable. In such embodiments, the electronics housing 15 can be routed to a cooler location away from the sensor 12, which will be discussed in more detail below.

Further, the electronics housing 15 may have any suitable shape. For example, as shown, the electronics housing 15 has a generally cylindrical shape. Moreover, as shown, the electronics housing 15 may be formed from two halves 33 secured together via a plurality of fasteners 35. As such, the cable 25 can be electrically coupled to the circuit board 32 by placing the cable 25 between the halves 33 and securing the halves 33 together. In addition, as shown in FIGS. 8-9, the electronics housing 15 may also include a pin connector 37 electrically coupled to the circuit board 32, e.g. opposite the cable connection.

Referring particularly to FIGS. 4 and 8-9, the electronics housing 15 is configured to house at least one amplifier 28 that is electrically coupled to the electrode 16. Since the amplifier 28 (and remaining electronics) of FIGS. 4-9 is separate from the sensor 12, the MCM sensor assembly 10 may have a higher operating temperature range of from about 250 degrees Celsius (° C.) to about 550° C., more preferably from about 370° C. to about 538° C. than the integrated sensor assembly of FIGS. 1-3. Further, it should be understood that the amplifier 28 may include any of the amplifiers as described herein such that the amplifier 28 is configured to detect or measure a particle level passing by the sensing face 22 of the sensor 12 as a function of the electron movement. In addition, as shown, the electronics housing 15 also houses the circuit board 32 that is electrically coupled to the sensor 12 via the cable 25. As mentioned, the circuit board 32 as described herein may include any suitable circuit board that mechanically supports and electrically connects the electronic components (such as the amplifier 28) to the sensor(s) 12. More specifically, certain circuit boards of the present disclosure may include conductive tracks, pads, and/or other features etched from sheets of metal, such as copper, that are laminated onto a non-conductive substrate.

The amplifiers 28 of the present disclosure are extremely sensitive and capable of more accurately detecting particle levels. More specifically, in certain embodiments, the amplifier 28 may include a leakage current of from about 1 femtoampere to about 5 femtoamperes, more preferably about 3 femtoamperes. Thus, the low leakage current facilitates DC coupling of the amplifier 28, which allows low frequency changes in particle levels to be captured. Further, the electrode 16 of the present disclosure may have an impedance of greater than about 1 G-Ohm, for example about 10 G-Ohm. As such, the high input impedance of the electrode 16 is configured to improve the sensor sensitivity to small changes in charge in the sensing face 22. Further, the high input impedance is also configured to improve the low frequency response of the electrostatic sensor 12 by preventing sensed charge from leaking away such that an output voltage cannot be produced. Thus, the electrostatic sensor(s) 12 of the present disclosure is capable of detecting from about one (1) part in seven (7) million by mass of particles.

Referring particularly to FIGS. 6 and 7, the electrostatic sensor(s) 12 may also include one or more insulators or insulation layers 34. For example, as shown in FIGS. 6 and 7, the electrostatic sensor(s) 12 may include a ceramic insulator 34 (such as alumina) between the electrode 16 and the outer housing 14. It should further be understood that any number of insulation layers may be employed at any suitable location within the sensor 12.

In addition, as shown, the electrostatic sensor 12 may further include one or more mechanical fasteners configured within the outer housing 14 between the ceramic insulator 34 and the cable 25. The mechanical fastener(s) may include flat washers, beveled washers, nuts, screws, or threads. More specifically, as shown in FIG. 7, the sensor 12 includes two inner flat washers 40 with an inner beveled washer 42 configured therebetween. Further, as shown, the sensor 12 also includes two outer flat washers with an outer beveled washer 46 configured therebetween. As such, the beveled washers 42, 46 are configured to act as a spring within the sensor 12 to relieve thermal stresses and/or to allow for expansion of the various components of the sensor 12 when operating at high temperatures. In addition, the inner and outer washer stacks may be separated or isolated from each other via gap 48 to allow movement at high temperatures without cracking the ceramic insulator 34. Similarly, another gap 49 may exist between the ceramic insulator 34 and the electrode 16 to further relieve thermal stresses therebetween. Still referring to FIG. 7, as mentioned, the mechanical fastener(s) may also include nut 41 adjacent to the inner washers 40, 42 that is configured for securing the electrode 16 within the outer housing 14.

Referring now to FIG. 10 a schematic diagram of one embodiment of circuit topology 50 that is suitable for the electrostatic sensor 12 according to the present disclosure is illustrated. As shown, the circuit 50 receives one or more sensor inputs from the electrostatic sensor 12. For example, the sensor inputs may be received from the electrode 16 of the sensor 12. The inputs are then transferred to a first amplifier 52. More specifically, the sensor input may first pass through a resistor $R_1$ so as to prevent and/or reduce electrostatic discharge (ESD) in the signal. Further, as shown, a large resistance resistor $R_2$ (e.g. about 10 G-ohms) is provided on the input path (designated as Pin 1) to bypass amplifier leakage current to ground. From Pin 2, a copy of the input signal is transferred to a second amplifier 54 at Pin 1. As shown, the signal travels through resistors $R_3$ and $R_4$, which set the gain of the signal. $R_5$ isolates the input capacitance of Pin 1 of amplifier 54 from the input signal. At least one of the resistors (i.e. $R_3$) may also include a capacitor $C_1$ configured in parallel therewith to limit the bandwidth of the amplifier 52. Capacitors $C_2$, $C_3$, $C_4$, and $C_5$ act as decoupling capacitors for the amplifiers 52 and 54. Resistors $R_6$ and $R_7$ protect amplifier outputs from ESD and also isolate the circuit from long external cables. A purpose of the second amplifier 54 is to guard the tiny sensor signal. For example, the second amplifier 54 may be configured with the same voltage and amplitude as the input to the first amplifier 52 but provides a low impedance source current. As such, as shown at Pin 3, the second amplifier 54 guards the sensor signal by tracking the sensor input voltage and diverting extraneous charges away from the sensor input. Thus, the amplifier configuration of the present invention includes a voltage follower with gain that is guarded by the second amplifier 54 tracking the sensor input voltage so as to guard it and produce a better signal to noise ratio.

The electrostatic sensors 12 described herein may have any suitable application. For example, in certain embodiments, the electrostatic sensors 12 of the present disclosure may be utilized in the aviation industry, such as an in aircraft gas turbine engine, as well as any other suitable engine types. More specifically, FIG. 11 illustrates a schematic cross-sectional view of one embodiment of a gas turbine engine 100 (high-bypass type) that may benefit from the electrostatic sensors 12 as described herein. As shown, the gas turbine engine 100 has an axial longitudinal centerline axis 102 therethrough for reference purposes. Further, as shown, the gas turbine engine 100 preferably includes a core gas turbine engine section generally identified by numeral 104 and a fan section 106 positioned upstream thereof. The core engine 104 typically includes a generally tubular outer casing 108 that defines an annular inlet 120. The outer casing 108 further encloses and supports a booster 122 for raising the pressure of the air that enters core engine 104 to a first pressure level. A high pressure, multi-stage, axial-flow compressor 124 receives pressurized air from the booster 122 and further increases the pressure of the air. The compressor 124 includes rotating blades and stationary vanes that have the function of directing and compressing air within the turbine engine 100. The pressurized air flows to a combustor 126, where fuel is injected into the pressurized air stream and ignited to raise the temperature and energy level of the pressurized air. The high energy combustion products flow from the combustor 126 to a first (high pressure) turbine 128 for driving the high pressure compressor 124 through a first (high pressure) drive shaft 130, and then to a second (low pressure) turbine 132 for driving the booster 122 and the fan section 106 through a second (low pressure) drive shaft 134 that is coaxial with the first drive shaft 130. After driving each of the turbines 128 and 132, the combustion products leave the core engine 104 through an exhaust nozzle 136 to provide at least a portion of the jet propulsive thrust of the engine 100.

The fan section 106 includes a rotatable, axial-flow fan rotor 138 that is surrounded by an annular fan casing 140. It will be appreciated that fan casing 140 is supported from the core engine 104 by a plurality of substantially radially-extending, circumferentially-spaced outlet guide vanes 142. In this way, the fan casing 140 encloses the fan rotor 138 and the fan rotor blades 144. The downstream section 146 of the fan casing 140 extends over an outer portion of the core engine 104 to define a secondary, or bypass, airflow conduit 148 that provides additional jet propulsive thrust.

From a flow standpoint, it will be appreciated that an initial airflow, represented by arrow 150, enters the gas turbine engine 100 through an inlet 152 to the fan casing 140. The airflow passes through the fan blades 144 and splits into a first air flow (represented by arrow 154) that moves through the conduit 148 and a second air flow (represented by arrow 156) which enters the booster 122.

The pressure of the second compressed airflow 156 is increased and enters the high pressure compressor 124, as represented by arrow 158. After mixing with fuel and being combusted in the combustor 126, the combustion products 160 exit the combustor 126 and flow through the first turbine 128. The combustion products 160 then flow through the second turbine 132 and exit the exhaust nozzle 136 to provide at least a portion of the thrust for the gas turbine engine 100.

Still referring to FIG. 11, the combustor 126 includes an annular combustion chamber 162 that is coaxial with the longitudinal centerline axis 102, as well as an inlet 164 and an outlet 166. As noted above, the combustor 126 receives an annular stream of pressurized air from a high pressure compressor discharge outlet 169. A portion of this compressor discharge air flows into a mixer (not shown). Fuel is injected from a fuel nozzle 180 to mix with the air and form a fuel-air mixture that is provided to the combustion chamber 162 for combustion. Ignition of the fuel-air mixture is accomplished by a suitable igniter, and the resulting combustion gases 160 flow in an axial direction toward and into an annular, first stage turbine nozzle 172. The nozzle 172 is defined by an annular flow channel that includes a plurality of radially-extending, circumferentially-spaced nozzle vanes 174 that turn the gases so that they flow angularly and impinge upon the first stage turbine blades of the first turbine 128. The first turbine 128 preferably rotates the high-pressure compressor 124 via the first drive shaft 130, whereas the low-pressure turbine 132 preferably drives the booster 122 and the fan rotor 138 via the second drive shaft 134.

The combustion chamber 162 is housed within the engine outer casing 108 and fuel is supplied into the combustion chamber 162 by one or more fuel nozzles 180. More specifically, liquid fuel is transported through one or more passageways or conduits within a stem of the fuel nozzle 180.

During operation, dust and other types of particles can be ingested by the gas turbine engine 100, e.g. from air entering the inlet 152. Dust and particle accumulation is a key input for engine analytics as these levels are important in evaluating engine service time, wear and tear, and/or other maintenance schedules. Thus, as mentioned, the electrostatic sensors 12 of the present disclosure are particularly useful for detecting dust and/or debris in such engines 100. As such, the electrostatic sensors 12 of the present disclosure may be located at any suitable location of the gas turbine engine 100. For example, the electrostatic sensors 12 of the present disclosure may be located within a borescope port, a compressor inlet 167 (FIG. 12), a compressor bleed pipe 170 (FIG. 13), a booster inlet 165 (FIG. 12), or a turbine or afterburner exit of the engine of the engine 100. More specifically, the electrostatic sensor 12 is capable of detecting very fine ice crystals, as can be encountered by a passenger aircraft at high altitude near the earth's equator. For such ice detection, the sensor 12 can be mounted at the booster inlet 165 or the compressor inlet 167. Further, the sensing face 22 can be sealed with a non-conductive epoxy coating to prevent water or melting ice from shorting out the electrode 16 to the body of the sensor 12.

More specifically, it should be understood that the electrostatic sensor 12 of the present disclosure may have any suitable shape to correspond with a desired mounting location. For example, in certain embodiments, the electrostatic sensor 12 may have a predetermined shape configured to fit in an existing location, a hole, or inlet of the gas turbine engine 100 such that the sensing face 22 is flush with an internal surface thereof. Particularly, as shown in FIGS. 1-3 and 12, the electrostatic sensor 12 may have a generally oblong or oval shape. Such a shape generally corresponds to an existing inlet location of the engine 100, such as but not limited to the compressor inlet 167 and/or the booster inlet 165. Alternatively, as shown in FIGS. 4-7 and 13-14, the electrostatic sensor 12 may have a generally cylindrical shape that corresponds to an inlet of the compressor bleed pipe 170 of the engine 100. Further, as particularly illustrated in FIG. 14, the sensor 12 may be mounted adjacent to the compressor bleed pipe 170 such that the sensing face 22 does not penetrate or intersect the flow path therein.

Referring now to FIGS. 12, 13, and 15, the MCM sensor assembly 10 may also be communicatively coupled to a controller 182 that is configured to receive the sensor signals generated by the electrode 16 of the sensor 12. More specifically, as shown in FIG. 15, there is illustrated a block diagram of one embodiment of suitable components that may be included in the controller 182 according to the present disclosure. As shown, the controller 182 may include one or more processor(s) 184 and associated memory device(s) 184 configured to perform a variety of computer-implemented functions (e.g., performing the methods, steps, calculations and the like and storing relevant data as disclosed herein). Additionally, the controller 182 may also include a communications module 188 to facilitate communications between the controller 182 and the electrostatic sensor(s) 12. Further, the communications module 188 may include a sensor interface 190 (e.g., one or more analog-to-digital converters) to permit signals transmitted from the sensor(s) 12 to be converted into signals that can be understood and processed by the processor(s) 184. It should be appreciated that the sensor(s) 12 may be communicatively coupled to the communications module 188 using any suitable means. For example, as shown in FIG. 15, the sensors 12 are coupled to the sensor interface 190 via a wired connection. However, in other embodiments, the sensors 12 may be coupled to the sensor interface 190 via a wireless connection, such as by using any suitable wireless communications protocol known in the art. As such, the processor(s) 184 may be configured to receive one or more signals from the sensors 12.

As used herein, the term "processor" refers not only to integrated circuits referred to in the art as being included in a computer, but also refers to a controller, a microcontroller, a microcomputer, a programmable logic controller (PLC), an application specific integrated circuit, and other programmable circuits. Additionally, the memory device(s) 186 may generally include memory element(s) including, but not limited to, computer readable medium (e.g., random access memory (RAM)), computer readable non-volatile medium (e.g., a flash memory), cloud storage, a floppy disk, a compact disc-read only memory (CD-ROM), a magneto-optical disk (MOD), a digital versatile disc (DVD) and/or other suitable memory elements. Such memory device(s) 186 may generally be configured to store suitable computer-readable instructions that, when implemented by the processor(s) 184, configure the controller 182 to perform various functions of the gas turbine engine 10.

Referring now to FIG. 16, a flow diagram of one embodiment of a method 200 for detecting particles in a gas turbine engine 100, e.g. an aircraft engine, is illustrated. As shown at 202, the method 200 includes providing at least one of the electrostatic sensors 12 as described herein in one or more locations in the gas turbine engine 100. Further, as shown at 204, the method 200 includes arranging the sensing face 22 of each sensor 12 in a particle flow path at the one or more locations. Thus, as shown at 206, the method 200 also includes determining, via the amplifier 28 of each sensor 12, a particle level within the gas turbine engine 100 as a function of electron movement in the electrode 16. As shown at 208, the method 200 includes generating, via a circuit board 32 closely coupled to the sensor 12, one or more signals indicative of the particle level in response to detecting charged particles.

In one embodiment, the method 200 may also include sending, via the circuit board 32 of the each of the electrostatic sensors 12, the signal(s) to the controller 182 of the gas turbine engine 100. As such, the sensors 12 described herein provide real-time, accurate particulate level data to a user.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they include structural elements that do not differ from the literal language of the claims, or if they include equivalent structural elements with insubstantial differences from the literal language of the claims.

What is claimed is:

1. An integrated sensor assembly, comprising:
at least one electrostatic sensor comprising:
an outer housing,
an electrode configured within the outer housing, wherein the electrode comprises an impedance of greater than about 1 G-Ohm, the electrode comprising a first end and a second end separated by a predetermined length, the second end comprising a sensing face that is substantially flush with an edge of the outer housing, the electrode comprising a plurality of electrons configured to respond to one or more charged particles that flow past the sensing face by moving either towards or away from the second end, and
an amplifier configured within the outer housing and electrically coupled to the electrode, wherein the amplifier comprises a leakage current of from about 1 femtoampere to about 5 femtoamperes the amplifier configured to detect a particle level flowing past the sensing face as a function of electron movement; and
a circuit board configured within the outer housing and electrically coupled to the sensor.

2. The sensor assembly of claim 1, wherein the sensing face of the electrode comprises a curved surface comprising a predetermined radius.

3. The sensor assembly of claim 1, wherein the amplifier comprises a wideband silicone on insulator (SOI) operational amplifier.

4. The sensor assembly of claim 1, wherein the amplifier comprises an operating temperature range of from about −55 degrees Celsius (° C.) to about 250° C.

5. The sensor assembly of claim 1, further comprising a controller configured to receive one or more signals from the circuit board indicative of the particle level.

6. The sensor assembly of claim 1, wherein the electrostatic sensor further comprises one or more insulators configured within the outer housing.

7. The sensor assembly of claim 1, wherein the outer housing of the electrostatic sensor comprises a predetermined shape configured to fit in one or more existing locations of an engine.

8. The sensor assembly of claim 7, wherein the one or more existing locations of the engine comprises at least one of a borescope port, a compressor inlet, a compressor bleed pipe, a booster inlet, or a turbine or afterburner exit of the engine.

9. The sensor assembly of claim 1, wherein the electrostatic sensor is configured to detect at least one of dust, debris, ice, sand, volcanic ash, or airborne particulates within a fluid medium, the fluid medium comprising at least one of air, water, oil, or fuel.

10. An integrated multi-chip module (MCM) sensor assembly, comprising:
at least one electrostatic sensor comprising:
an outer housing,
an electrode configured within the outer housing, wherein the electrode comprises an impedance of greater than about 1 G-Ohm, the electrode comprising a first end and an opposing second end having a sensing face, the electrode comprising a plurality of electrons configured to respond to one or more charged particles that flow past the sensing face by moving either towards or away from the second end, and
an amplifier configured within the outer housing and electrically coupled to the electrode, wherein the amplifier comprises a leakage current of from about 1 femtoampere to about 5 femtoamperes, the amplifier configured to detect a particle level flowing past the sensing face as a function of electron movement; and a circuit board electrically coupled to the sensor.

11. A sensor assembly, comprising:
at least one electrostatic sensor comprising:
an outer housing,
an electrode configured at least partially within the outer housing, wherein the electrode comprises an impedance of greater than about 1 G-Ohm, the electrode comprising a first end and a second end separated by a predetermined length, the first end secured within the outer housing, the second end comprising a sensing face that extends beyond an edge of the outer housing, the electrode comprising a plurality of electrons configured to respond to one or more charged particles that flow past the sensing face by moving either towards or away from the second end, and
an amplifier configured within the outer housing and electrically coupled to the electrode, wherein the amplifier comprises a leakage current of from about 1 femtoampere to about 5 femtoamperes, the amplifier configured to detect a particle level flowing past the sensing face as a function of electron movement; and
a circuit board electrically coupled to the sensor via a cable.

12. The sensor assembly of claim 11, wherein the second end of the electrode comprises a curved surface comprising a predetermined radius.

13. The sensor assembly of claim 12, wherein the curved surface comprises one or more protrusions.

14. The sensor assembly of claim 11, wherein the amplifier comprises a wideband silicone on insulator (SOI) operational amplifier.

15. The sensor assembly of claim 11, wherein the amplifier comprises an operating temperature range of from about −55 degrees Celsius (° C.) to about 250° C., and the sensing face comprises an operating temperature range of from about −55 degrees Celsius (° C.) to about 550° C.

16. The sensor assembly of claim 11, wherein the electrostatic sensor further comprises one or more insulators configured within the outer housing.

17. The sensor assembly of claim 16, wherein the electrostatic sensor further comprises one or more mechanical fasteners configured within the outer housing between the one or more insulators and the cable.

18. The sensor assembly of claim 17, wherein the one or more mechanical fasteners comprise at least one of flat washers, beveled washers, nuts, screws, or threads.

19. The sensor assembly of claim 11, wherein the electrostatic sensor is configured to detect at least one of dust, debris, ice, sand, volcanic ash, or airborne particulates within a fluid medium, the fluid medium comprising at least one of air, water, oil, or fuel.

* * * * *

UNITED STATES PATENT AND TRADEMARK OFFICE
CERTIFICATE OF CORRECTION

| | | |
|---|---|---|
| PATENT NO. | : 9,651,469 B1 | Page 1 of 1 |
| APPLICATION NO. | : 15/375882 | |
| DATED | : May 16, 2017 | |
| INVENTOR(S) | : Weickert et al. | |

It is certified that error appears in the above-identified patent and that said Letters Patent is hereby corrected as shown below:

On the Title Page

On Page 2, in Item (56), under "OTHER PUBLICATIONS", in Column 1, Line 1, delete "Wetckert" and insert -- Weickert --, therefor.

In the Specification

In Column 9, Line 43, delete "FIG. 10" and insert -- FIG. 10, --, therefor.

In Column 12, Line 17, delete "device(s) 184" and insert -- device(s) 186 --, therefor.

In Column 12, Line 54, delete "engine 10." and insert -- engine 100. --, therefor.

In the Claims

In Column 13, Line 41, in Claim 1, delete "femtoamperes" and insert -- femtoamperes, --, therefor.

Signed and Sealed this
Seventeenth Day of October, 2017

Joseph Matal
*Performing the Functions and Duties of the*
*Under Secretary of Commerce for Intellectual Property and*
*Director of the United States Patent and Trademark Office*